US006803504B2

(12) United States Patent
Bilyeu

(10) Patent No.: US 6,803,504 B2
(45) Date of Patent: Oct. 12, 2004

(54) SOYBEAN VARIETY S02-AP98041-2-333-01

(75) Inventor: Keith Bilyeu, Ames, IA (US)

(73) Assignee: Advanta U.S.A., Inc., Slater, IA (US)

( * ) Notice: Subject to any disclaimer, the term of this patent is extended or adjusted under 35 U.S.C. 154(b) by 118 days.

(21) Appl. No.: 10/098,191

(22) Filed: Mar. 13, 2002

(65) Prior Publication Data

US 2003/0121076 A1 Jun. 26, 2003

Related U.S. Application Data

(63) Continuation-in-part of application No. 09/816,791, filed on Mar. 23, 2001.

(51) Int. Cl.[7] .............................. A01H 1/00; C12N 5/14
(52) U.S. Cl. ........................ 800/312; 435/415; 435/418; 435/419; 800/260; 800/278; 800/279; 800/288; 800/295; 800/298

(58) Field of Search .................................. 435/415, 418, 435/419; 800/260, 278, 279, 288, 295, 298

(56) References Cited

U.S. PATENT DOCUMENTS 5,872,303 A * 2/1999 Rhodes

* cited by examiner

Primary Examiner—Phuong T. Bui
(74) Attorney, Agent, or Firm—Dana S. Rewoldt, Esq.

(57) ABSTRACT

The present invention is in the field of soybean variety S02-AP98041-2-333-01 breeding and development. The present invention particularly relates to the soybean variety S02-AP98041-2-333-01 and its progeny, and methods of making S02-AP98041-2-333-01.

13 Claims, No Drawings

SOYBEAN VARIETY S02-AP98041-2-333-01

The present invention is a Continuation-in-Part (C-I-P) claiming the benefit of the utility U.S. patent application Ser. No. 09/816,791 filed on Mar. 23, 2001 under 35 US 120.

THE FIELD OF THE INVENTION

The present invention is in the field of soybean variety S02-AP98041-2-333-01 breeding and development. The present invention particularly relates to the soybean variety S02-AP98041-2-333-01 and its progeny, and methods of making.

BACKGROUND OF THE INVENTION

The breeding and development of crops has been ongoing across the last 1000 years. The pace of this development in soybeans, as an animal foodstuff and as an oil seed has dramatically increased in the last one hundred years. Planned programs of plant breeding have increased the growth, yield and environmental hardiness of the soybean germplasm. Due to the sexual reproduction traits of the soybean the plant is basically self-pollinating. A self-pollinating plant permits pollen from one flower to be transferred to the same or another flower of the same plant. Cross-pollination occurs when the flower is pollinated with pollen from a different plant. This is a rare occurrence in nature.

Thus the growth and development of new soybean germplasm requires intervention by the breeder in the pollination of the soybean. The breeders' selections of methods of intervening in the pollination depend on the type of trait that is being selected. Soybeans are developed for a number of different types of traits morphological (form and structure), phenotypical, for growth habit, daylength temperature requirements to initiate floral or reproductive development yield. The genetic complexity of the trait drives the breeding method. Backcross breeding is employed when the cultivar that is being bred has a fairly full profile of desirable traits, but lack one or two traits that are highly inheritable. Backcrossing is often employed to move disease resistance, insect resistance and transgenes (hereinafter DNA which are introduced into the original ancestor germplasm by a transformation method) into other varieties.

When the variety is being employed to develop a new variety or an improved variety the selection methods include pedigrees, recurrent, modified and mass selection and back-crossing. Each of these selection techniques is employed with the efficiency of the breeding procedure as the driver. The breeding procedure requires a continuous evaluation of the success of the breeding program. The success is measured by yield increase, commercial appeal and environmental adaptability of the developed germplasm.

New varieties must be tested thoroughly to compare the development with the commercially available soybeans. This testing usually requires at least two years and up to six years of comparisons with other commercial soybeans. Varieties that lack the entire desirable package of traits can be used as parents in new populations for further selection. The breeding and associated testing process is 8 to 12 years' progression toward a new variety. Thousands of lines are produced and limited lines are selected in each step of the process. Thus the breeding system is like a funnel with numerous lines and selections in the first few years and fewer and fewer lines in the middle years until one line is selected for the final development testing.

The selected line or variety will be evaluated for it's the growth and development and yield. These traits of a soybean are a result of the varieties genetic potential interacting with its environment. All varieties have a maximum yield potential that is predetermined by its genetics. This hypothetical potential for yield is only obtained when the environmental conditions are perfect. Since perfect growth conditions do not exist field experimentation is necessary to provide the environmental influence and to measure its effect on the development and yield of the soybean. The breeder attempts to select for good soybean yield potential under a number of different environmental conditions.

Selecting for good soybean yield potential under a number of different environmental conditions is a process that requires planning, analysis of data in a number of seasons. Identification of the varieties that carry a superior combination of traits that provides this consistent yield potential is a complex science. Other plant traits, unusual weather patterns, diseases, and insect damage often mask the genotypic traits. One widely employed method of identifying a superior plant is to observe its performance relative to commercial and experimental plants in replicated studies. These types of studies give more certainty to the genetic potential and value of the plant.

The goal of the soybean plant breeder is to produce unique and new soybeans and progeny of the soybeans. To accomplish this the plant breeder painstakingly crosses two or more varieties or germplasm. Then the results of this cross is repeatedly selfed or backcrossed to produce new genetic patterns. Additionally, the breeder can introduce mutations into the genetic material. These can alter herbicide resistance, fatty acid compositions, and amino acid compositions of the seeds and the like. Fortunately, through transformation in combination with breeding the plant breeder can alter or introduce some genetic alleles into the breeding material.

These capabilities are widening the potential uses and markets for the various products and by-products of oil seed plants such as soybean. One of the products of soybeans is the oil of the seed. Soybean oil is employed in a number of retail products. Soybean meal is also used in food and animal feedstuffs. The traits a breeder selects for can be driven by the ultimate goals of the end user of the product. Thus if the goals of the end user is to produce an oil with a high level of oleic acid and a lower level of linoleic acid then the breeder may drive the genetics toward levels of fatty acids and accept some lesser yield potentials or other less desirable agronomic traits.

Regardless of the market characteristics of the plant most breeding proceeds along a similar path on a yearly basis. The breeder annually selects the germplasm to advance on into further development. This germplasm is grown in different locations at different altitudes, in different climates and subjected to different soil conditions. Based on the datum collected from these tests individual plants are selected during the end of the growing season. Due to the number of genes within each chromosome millions of genetic combinations exist in the breeders' experimental soybean material. This genetic diversity is so vast that a breeder cannot produce the same two cultivars twice using the exact same material. Thus the developing a single variety of useful commercial soybean germplasm is highly unpredictable, and requires intensive research.

The development of new soybeans comes through breeding techniques such as recurrent selection, mass selections, backcrossing, single seed descent and multiple seed procedure that is used to save labor costs. Other breeding methods are taught in several soybean textbooks.

The development of soybean cultivars most often requires the development of hybrid crosses (some exceptions being initial development of mutants directly through the use of the mutating agent or transformants made directly through transformation methods) and the selection of progeny therefrom. Hybrids can be achieved by manual manipulation of the sexual organs of the soybean or by the use of male sterility systems. The breeder attempts to identify true hybrids by a readily identifiable trait. These hybrids are then selected and repeatedly selfed and selected to form new homozygous lines from the heterozygous hybrids.

Outcrossing to a number of different parents creates breeding populations of fairly heterozygous populations. These populations are produced and used in pedigree breeding and recurrent selection. Pedigree breeding is commonly used with two parents which possess favorable, complementary traits. The parents are crossed to form a F1 hybrid. The progeny of the F1 hybrid is selected from this the best individuals F2 are selected; this selection process is repeated in the F3 and F4 generations. The inbreeding is carried forward and at F5–F7 the best lines are selected and tested in the development stage for potential usefulness.

Mass and recurrent selection can be used to improve populations. Several parents are intercrossed and plants are selected based on selected characteristics like superiority or excellent progeny.

In backcross breeding a genetic allele or loci is transferred into a desirable homozygous recurrent parent. The trait is in the donor parent and is tracked into the recurrent parent. The resultant plant is like the recurrent parent with the new desired allele or loci.

The single-seed descent method involves use of a segregating plant population for harvest of one seed per plant. Each seed sample is planted and the next generation is formed. When the F2 lines are advanced to F6 each plant will be derived from a different F2. The population will decline due to failure of some seeds, so not all F2 plants will be represented in the progeny.

Soybean *Glycine max* (L) is an important oil seed crop and a valuable field crop.

SUMMARY OF THE INVENTION

One embodiment of the invention relates to seed of a soybean cultivar designated S02-AP98041-2-333-01. And the plant, or parts including ovule, a tissue culture of regenerable cells, cells or protoplasts being from a tissue selected from the group consisting of leaves, pollen, embryos, meristematic cells, roots, root tips, anthers, flowers, seeds, stems and pods and pollen thereof, produced by growing the seed.

The invention in one aspect covers a soybean plant, or parts thereof, having all of the physiological and morphological characteristics of the soybean plant.

Another aspect of this invention is the soybean plant seed or derived progeny which contains a transgene (which include DNA whether or not it is a full or partial sequence) affecting herbicide resistance, insect resistance, resistance to disease, nematodes, male sterility, and altered oil or amino acids or other nutritional quality.

The present invention further covers a method for producing a soybean seed with the steps of crossing at least two parent soybean plants and harvesting the hybrid soybean seed, wherein at least one parent soybean plant is the present invention. In another aspect of the invention covers the hybrid soybean seed and the progeny soybean plant and resultant seed, or parts thereof from the hybrid seed or plant or its progeny.

In an additional aspect the invention covers a method for producing a soybean progeny from the invention by crossing soybean line S02-AP98041-2-333-01 with a second soybean plant to yield progeny soybean seed and then growing progeny soybean seed to develop a derived soybean line.

Yet another aspect of the invention covers a method for a breeding program using plant breeding techniques which employ the soybean plant S02-AP98041-2-333-01 as plant breeding material and performing breeding by selection techniques, backcrossing, pedigree breeding, marker enhanced selection, mutation and transformation.

DETAILED DESCRIPTION
Soybean Data Collection

| Core Traits | Abbr. | Description | Timing | Scale |
|---|---|---|---|---|
| Hila | HC | Phenotypic color; All experiments. | | G = Gray; BR = Brown; IB = Imperfect Black; Bl = Black; Y = Yellow; BF = Buff; IY = Imperfect Yellow; X = Mix |
| Flower | FC | Phenotypic color; All experiments. | | W = White; P = Purple; X = Mix |
| Pod | POD | Phenotypic color; All experiments. | | T = Tan; B = Brown; X = Mixed |
| Pubescence | PUB | Phenotypic color; All experiments. | | G = Gray; T = Tawny; LT = Light Tawny; X = Mixed |
| GWT | GWT | Grain weight/plot | Harvest | Pounds |
| H2O | H20 | Grain moisture/plot | Harvest | % moisture |
| Necessary Traits Y3 & Y4 See also "Trait Definitions" | Abbr. | | Timing | Scale |
| Hypocotyl Elongation | HYPO | Replicated Nursery 4 locations/test | May to June | 1 to 5 (1 = best) |
| Seedling Establishment | EMG | | VE-V1 | 1 to 5 (1 = best) |

-continued

| | | | | |
|---|---|---|---|---|
| Maturity | MAT | 4 locations/test | | Taken in days after Aug. 31 |
| Plant Height | PLTHT | 4 locations/test | Harvest | Taken in inches |
| Branching | BR | 4 locations/test | R8-Harvest | 1 to 5(1 = no branch) |

| Agronomic Traits See also "Trait Definitions" | Abbr. | Opportunistic | Timing | Scale |
|---|---|---|---|---|
| Green Lodging | GLOD | Where differential occurs. | R5 to R6 | 1 = All erect<br>2 = 67°<br>3 = 45°<br>4 = 22°<br>5 = 0° |
| Stem Lodging | LOD | Where differential occurs | Harvest | 1 = All erect<br>2 = 67°<br>3 = 45°<br>4 = 22°<br>5 = 0° |
| Shatter | SHAT | Where differential occurs | Harvest | 1 to 5 (1 = best) |

| Opportunistic Disease Ratings | Abbr. | Key Maturities | Scale |
|---|---|---|---|
| Phytophthora Root Rot | PFT | All | 1 to 5 (1 = best) |
| Brown Stem Rot | BSR | G0 to EGIII | 1 to 5 (1 = best) |
| Sclerotinia White Mold | SWM | G0 to EGIII | 1 to 5 (1 = best) |
| Sudden Death Syndrome | SDS | EGII to GVII | 1 to 5 (1 = best) |
| Stem Canker | STMC | MGII to GVII | 1 to 5 (1 = best) |
| Charcoal Rot | CROT | LGIII to GVII | 1 to 5 (1 = best) |
| Frog Eye | FROG | EGIII to GVII | 1 to 5 (1 = best) |

| Disease Nurseries | Abbr. | Path | Timing | Scale |
|---|---|---|---|---|
| Iron Deficiency Chlorosis | IDC | Internal Field Nursery | June–July | 1 to 5 (1 = best) |
| Soybean Cyst Nematode | SCN | Race 3 Internal Nursery, | Nov–April 30d cycle | R—MR—MS—S |
| Phytophthora Root Rot | PFT or PGR | | | 1 to 5 (1 = best) for field tolerance and 1a, 1b, 1c, 1k, etc for specific genes. |
| Sudden Death Syndrome | SDS | | | Disease Severity Index or DSI. |
| Brown Stem Rot | BSR | | | 1 to 5 (1 = best) |
| Root Knot Nematode | RKN | | | R—MR—MS—S |
| Stem Canker | STMC | | | 1 to 5 (1 = best) |

| Herbicide Evaluation | Abbr. | | | |
|---|---|---|---|---|
| Sulfentrazone | SULF | | | Sensitive, Tolerant |
| Metributzin | MET | | | Sensitive, Tolerant |

***All data to default to a "." (period) when data is not observed

Trait Definitions

Hypocotyl Elongation (HYPO) A rating of a variety's hypocotyl extension after germination when planted at a 5" depth in sand and maintained a warm germination environment for 10 days.

Seedling Establishment (EMG) A rating of the uniform establishment and growth of seedlings.

Maturity (MAT) The number of days after August 31 when 95% of the main stem pods in the plot have reached their mature color.

Plant Height (PLTHT) The average measured plant height in inches.

Branching (BRANCH) Rating of the number of branches and their relative importance to yield. Taken at growth expressive locations.

Green Lodging (GLODGE) Rating based on the average of plants leaning from vertical in R5 to R6 stage.

Stem Lodging (LODGE) Rating based on the average of plants leaning from vertical at harvest.

Shatter (SHAT) Rating of pre-harvest loses based on amount of plants with open pods.

Iron Deficiency Chlorosis (IDC) A composite rating of Yellow Flash, Green-up, and Stunting in HpH soil.

Phytophthora Root Rot (PGR) or (PFT) Greenhouse pot—root dip method for PFT and hypodermic needle method for PGR.

Root Knot Nematode (RKN) Greenhouse screen—30 day screen using infested soil. Rating Scale based upon female reproduction index on a susceptible check set where <10%=R; <30%=MR; <60%=MS; >60%=S.

Stem Canker (STC) Based on a number of lesions, scale 1–5.

Sulfentrazone (SULF) Authority$_{TM}$ (commercial herbicide) Greenhouse nursery rating damage of multiple rates.

Metributizin (MET) Greenhouse nursery rating damage of multiple rates.

Definitions of Staging Development

The plant development staging employed divides stages as vegetative (V) and reproductive (R). This system accurately identifies the stages of a soybean plant. However, all plants in a given field will not be in the stage at the same time. Each specific V or R stage is defined as when 50% or more of the plants in the field are in or beyond that stage.

The first two stages of V are designated a VE (emergence) and VC (cotyledon stage). Subdivisions of the V stages are then designated numerically as V1, V2, V3 through V (n). The last V stage is designated as V (n), where (n) represents the number for the last node stage of the specific variety. The (n) will vary with variety and environment. The eight subdivisions of the reproductive stages (R) states are also designated numerically. R1=beginning blom; R2=full bloom; R3=beginning pod; R4=full pod; R5=beginning seed; R6=Full Seed; R7=beginning maturity; R8=Full maturity.

BROWN STEM ROT (BSR)—This disease is caused by the fungus *Phialophora gregata*. The disease is a late-season, cool-temperature, soilborne which in appropriate favorable weather can cause up to 30 percent yield losses in soybean fields. For purposes of these tests the information is gathered in a greenhouse with a plant in a pot then a root dip procedure is employed.

SUDDEN DEATH SYNDROME (SDS)—This disease is caused by slow-growing strains of *Fursarium solani* that produce bluish pigments in culture. The disease is mid- to late season soil borne and occurs in soybean fields with high yield potential. Yield losses may be total/severely affected fields. Sudden Death Syndrome (SDS) is based on leaf area affected, scale used for these tests is 1–5.

SOYBEAN CYST NEMATODE—The Soybean Cyst Nematode (SCN) *Heterodera glycines*, is a small plant—parasitic roundworm that attacks the roots of soybeans. Soybean Cyst Nematode (SCN) for purposes of these tests are done as a greenhouse screen—30 day screen using infested soil. Rating Scale based upon female reproduction index on a susceptible check set where <10%=R; <30%=MR; <60%=MS; >60%=S. In priority order, the screening races include: 3, 14, & 1.

MATURITY DATE. Plants are considered mature when 95% of the pods have reached their mature color. The number of days are either calculated from September 1 or from the planting date. (MR#) wherein # equals days.

RELATIVE MATURITY GROUP(RM). Industry Standard for varieties groups, based day length or latitude. Long day length (northern areas in the Northern Hemisphere) are classified as (Groups 000,00,0,) and extend to very short day lengths variety groups (southern areas in Northern Hemisphere) classified as (Groups VII, VIII, IX).

SEED YIELD (Bushels/Acre). The yield in bushels/acre is the actual yield of the grain at harvest.

SHATTERING. The rate of pod dehiscence prior to harvest. Pod dehiscence involves beans dropping out of the pods. Shatter (SHAT) for these tests the rating of pre-harvest loses is based on amount of plants with open pods.

PLANT. Means the plant cells, plant protoplasts, plant cells of tissue culture from which soybean plants can be regenerated, plant calli, plant clumps, and plant cells that are intact in plants or parts of plants, such as pollen, nodes, roots, flowers, seeds, pods, leaves, stems, and the like.

The present invention is S02-AP98041-2-333-01. S02-AP98041-2-333-01 is a 2.6 relative maturity. It is best adapted to regions in the U.S. (though it can be used in other countries adapted for soybeans) of central Iowa, northern Illinois, northern Indiana, southern Michigan, northern Ohio, northern Nebraska, and extreme southern South Dakota. The traits of the invention are listed below.

| TRAIT | |
|---|---|
| RM | 2.6 |
| HR-herbicide resistance | RR = Round Up Ready resistance transgene |
| Flower Color | purple |
| Pubescene Color | T |
| Pod Color | Tan |
| Hila Color | Black |
| Seed/Lb | 2700–3000 |
| Lust | Dull |
| Perox | Positive |
| Phytophthora Root Rot | 3.1 |
| RKN | — |
| Brown Stem Rot | — |
| Iron Deficiency Chlorosis | 2.5 |
| Sclerotinia White Mold | — |
| Sudden Death Syndrome | — |
| Stem Canker | — |
| Charcoal Rot | — |
| Frog Eye | — |
| SCN | R3-MR14 |
| PGR | 1k |

The instant invention provides methods and composition relating to plants, seeds and derivatives of the soybean cultivar S02-AP98041-2-333-01. Soybean cultivar S02-AP98041-2-333-01 has superior characteristics. The S02-AP98041-2-333-01 line has been selfed sufficient number of generations to provide a stable and uniform plant variety.

Cultivar S02-AP98041-2-333-01 shows no variants other than expected due to environment or that normally would occur for almost any characteristic during the course of repeated sexual reproduction. Some of the criteria used to select in various generations include: seed yield, lodging resistance, emergence, appearance, disease tolerance, maturity, plant height, maturity and shattering data.

The inventor believes that S02-AP98041-2-333-01 is similar to the comparison varieties. However, as shown in the tables, S02-AP98041-2-333-01 differs from these cultivars.

Direct comparisons were made between S02-AP98041-2-333-01 and these competing commercial varieties. Traits measured included yield, maturity, moisture, lodging, plant height, field emergence, protein and oil. The results of the comparison are presented in below. The number of tests in which the varieties were compared is shown. The deviation or difference of the results, T-value and the traits which showed a significant difference and the level of that significance are in the first table and the second Table indicates the advantage positive number or disadvantage negative of the present invention when compared to the commercial lines.

The present invention S02-AP98041-2-333-01 can carry genetic engineered recombinant genetic material to give improved traits or qualities to the soybean. For example, but not limitation the present invention can carry, the glyphosate resistance gene for herbicide resistance as taught in the Dekalb U.S. patent or a oxalate oxidase (Ox Ox) gene as taught in PCT/FR92/00195 Rhone Polunc and/or an Ox Decarboxylate gene for disease resistance or genes designed to alter oil such as desaturase genes or amino acid characteristics such as desaturase genes.

The earlier filed invention AP98041-2-333 had a mixed pod color. The present invention S02-AP98041-2-333-01 was selected from AP98041-2-333 to have a tan pod color only. S02-AP98041-2-333-01 differs AP98041-2-333 which only differs in that the pod color is tan and not mixed. When S02-AP98041-2-333-01 is employed in a trialling for a number of characteristics, S02-AP98041-2-333-01 does not differ from AP98041-2-333 except for this pod color trait. These tests allow the usefulness of the invention to be shown in light of the environmental genetic interactions.

so that the variety has a tan pod color. The data concerning agronomic traits and quality traits does not appear to vary due to the selection for a specific pod color. The tan pod variety is designed as S02-AP98041-2-333-01. The tan pod variety was compared with D294RR/N and the present invention showed better moisture at harvest but significantly different yields in this location.

| Ent | Yld | Moist | App | Branch | BSR | E |
|---|---|---|---|---|---|---|
| AP98041-2-333 | 53.2 | 11.1 | 2.2 | 2 | . | . |
| AG2201 | 50.8 | 10.9 | 2.8 | 2 | . | . |
| # REPS | 44 | 45 | 20 | 2 | 0 | 0 |
| Diff | 2.4 | 0.2 | −0.7 | 0 | . | . |
| Std | 8.8 | 0.7 | 1.2 | 0 | . | . |
| T-val | 1.77 | 1.73 | −2.46 | . | . | . |
| Prob | 0.084* | 0.091* | 0.024** | . | . | . |

| Ent | Lg | Mat | Pltht | PRR | Shatter | IDC |
|---|---|---|---|---|---|---|
| AP98041-2-333 | 1.5 | 16.5 | 31.3 | . | . | . |
| AG2201 | 2 | 11.9 | 33.5 | . | . | . |
| # REPS | 26 | 14 | 28 | 0 | 0 | 0 |
| Diff | −0.5 | 4.6 | −2.2 | . | . | . |
| Std | 1.5 | 2.6 | 4.7 | . | . | . |
| T-val | −1.86 | 6.52 | −2.48 | . | . | . |
| Prob | 0.075* | 0*** | 0.02** | . | . | . |

*Significant at the .10 level
**Significant at the .05 level
***Significant at the .01 level
E = Emergence
Moist = Moisture
App = Appearance
BSR = Brown Stem Rot
Yld = Yield
Lg = Lodging
Mat = Maturity in days after September 1
Pltht = Plant height
PRR = Phytophthora Root Rot
Shatter = Pod breakage
IDC = Iron Deficiency Chlorosis The variety with the mixed pod is providing yield that is statistical significant over the commercial line with a slightly higher moisture.

Although the present invention has a slightly later maturity in days after September 1 then the commercial line, it has significantly less lodging than does the commercial line in accordance to this test in these environmental conditions.

This AP98041-2-333 invention was compared with D221RR/N and D224RR/N for certain grain quality traits. The AP98041-2-333 shows the same moisture as D221RR/N and slightly higher moisture than D224RR/N. The protein level of the present invention provide an advantage over D221RR/N and the oil of AP98041-2-333 shows

| Ent | Yld | Moist | App | Branch | BSR | E | Lg | Mat | Pltht | IDC |
|---|---|---|---|---|---|---|---|---|---|---|
| S02-AP98041-2-333-01 | 51.1 | 11.6 | 2.3 | 2.5 | | 3 | 2.7 | 27 | 30.7 | 3.7 |
| D294RR/N | 55.1 | 12.1 | 3.3 | 3 | | 3 | 2.7 | 31.7 | 39.3 | 4.5 |
| # LOCS | 8 | 8 | 3 | 1 | 0 | 1 | 7 | 6 | 5 | 4 |
| Diff | −4 | −0.4 | −1 | −0.5 | | 0 | 0 | −4.7 | −8.7 | −0.8 |
| Std | 4.2 | 1.4 | 0.5 | | | | 1 | 2.5 | 2.3 | 0.9 |
| T-val | −2.73 | −0.81 | −3.46 | | | | −0.1 | −4.61 | −8.53 | −1.73 |
| Prob | 0.029** | 0.445 | 0.074* | | | | 0.926 | 0.006*** | 0.001*** | 0.182 |

*Significant at the 0.01 level
**Significant at the 0.05 level
***Significant at the 0.01 level This S02-AP98041-2-333-01 invention is the same as AP98041-2-333 except that a tan pod was selected and bred an advantage over the oil levels produced in the beans of D224RR/N.

| VARIETY | # | MOIST | ADV | PROTEIN | ADV | OIL | ADV | SDS/ Per LB | ADV |
|---|---|---|---|---|---|---|---|---|---|
| AP98041-2-333 | 2 | 6.7 | 0 | 41.75 | 1.59 | 21.28 | −0.17 | 2874 | −361.5 |
| D221RR/N | 2 | 6.7 | | 40.16 | | 21.45 | | 3235.5 | |
| AP98041-2-333 | 3 | 7.1 | 0.2 | 41.91 | −0.5 | 21.29 | 0.27 | 2886 | −322 |
| D294RR/N | 3 | 6.8 | | 42.37 | | 21.03 | | 3208 | |

The data for the S02-AP98041-2-333-1 was taken in a different year and at different locations. Thus it cannot be directly compared with the data above. The present invention showed:

| Var | Sds Per Lb | Protein | Oil |
|---|---|---|---|
| S02-AP98041-2-333-01 | 2300–3300 | 35.90 | 17.70 |

These numbers of seeds per lb and protein and oil are similar to AP98041-2-333 when the tests are run under the same locations and conditions.

This invention also is directed to methods for producing a new soybean plant by crossing a first parent plant with a second parent plant wherein the first or second parent plant is the present invention. Additionally, the present invention maybe used in the variety development process to derive progeny in a breeding population or crossing. Further, both first and second parent plants can come from the soybean line S02-AP98041-2-333-01. A variety of breeding methods can be selected depending on the mode of reproduction, the trait, and the condition of the germplasm. Thus, any such methods using the S02-AP98041-2-333-01 are part of this invention: selfing, backcrosses, recurrent selection, mass selection and the like.

Transformation methods are means for integrating new genetic coding sequences (transgenes) into the plant's genome by the incorporation of these sequences into a plant through man's assistance. Many dicots including soybeans can easily be transformed with Agrobacterium. The most common method of transformation after the use of agrobacterium is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art. The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

After the transformation of the plant material is complete, the next step is identifying the cells or material, which has been transformed. In some cases, a screenable marker is employed such as the beta-glucuronidase gene of the uidA locus of E. coli. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly effected by the toxic agent by having slower growth rates. If the transformed material was cell lines then these lines are regenerated into plants. The cells' lines are treated to induce tissue differentiation. Methods of regeneration of cellular are well known in the art. The plants from the transformation process or the plants resulting from a cross using a transformed line or the progeny of such plants are transgenic plants that carry the transgene.

Deposit Information

A deposit of the Advanta USA, Inc. Seed soybean cultivar S02-AP98041-2-333-01 disclosed above and recited in the appended claims will be made with the American Type Culture Collection (ATCC), 10801 University Boulevard, Manassas, Va. 20110. The date of deposit was XXXX. The deposit of 2,500 seeds maintained by Advanta USA Inc. since prior to the filing date of this application. All restrictions upon the deposit have been removed, and the deposit is intended to meet all of the requirements of 37 C.F.R. §§1.801–1.809. The ATCC accession number is XXX. The deposit will be maintained in the depository for a period of 30 years, or 5 years after the last request, or for the effective life of the patent, whichever is longer, and will be replaced as necessary during that period.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

What is claimed is:

1. A soybean seed designated S02-AP98041-2-333-01, a sample of said seed deposited under ATCC Accession No. PTA-5652.

2. A plant, or parts thereof, produced by growing the seed of claim 1.

3. Pollen of the plant of claim 2.

4. A soybean plant, or parts thereof, having all of the physiological and morphological characteristics of the soybean plant of claim 2.

5. A tissue culture of regenerable cells of the soybean plant of claim 2.

6. The tissue culture according to claim 5, wherein the cells are obtained from the group consisting of leaves, pollen, embryos, meristematic cells, roots, root tips, anthers, stomatal cells, flowers, seeds, stems and pods.

7. A soybean plant regenerated from the tissue culture of claim 5, having all of the morphological and physiological characteristics of soybean cultivar S02-AP98041-2-333-01.

8. A method for producing a soybean seed comprising crossing two soybean plants and harvesting the resultant soybean seed, wherein at least one soybean plant is the soybean plant of claim 2.

9. A method for producing a hybrid soybean comprising crossing the soybean plant according to claim 2 with a second soybean plant and harvesting the resultant hybrid soybean seed.

10. A method for producing a S02-AP98041-2-333-01-derived soybean plant, comprising:
 a) crossing soybean line S02-AP98041-2-333-01, a sample of said line deposited under ATCC Accession No. PTA-5652, with a second soybean plant to yield progeny soybean seed; and
 b) growing said progeny soybean seed to yield said S02-AP98041-2-333-01-derived soybean plant.

11. The method of claim 8, wherein the second soybean plant is transgenic.

12. The method of claim 11 wherein the transgenic soybean plant contains genetic material selected from the group consisting of herbicide resistance, insect resistance, resistance to disease and male sterility.

13. The method of claim 12 wherein the resistance to disease is through an oxalate oxidase encoding polynucleotide sequence or an oxalate decarboxylate encoding polynucleotide sequence.

* * * * *